United States Patent [19]

Hanson et al.

[11] Patent Number: 5,700,669

[45] Date of Patent: Dec. 23, 1997

[54] ENZYMATIC HYDROLYSIS METHOD FOR THE CONVERSION OF C-7 SUGAR TO C-7 HYDROXYL TAXANES

[75] Inventors: Ronald L. Hanson, Morris Plains; Ramesh N. Patel, Bridgewater; Laszlo J. Szarka, East Brunswick, all of N.J.

[73] Assignee: Bristol-Myers Squibb Company, Princeton, N.J.

[21] Appl. No.: 421,017

[22] Filed: Apr. 12, 1995

Related U.S. Application Data

[63] Continuation of Ser. No. 181,633, Jan. 13, 1994, abandoned.

[51] Int. Cl.$^6$ .................................................. C12P 17/02
[52] U.S. Cl. ..................... 435/123; 435/252.5; 435/252.1
[58] Field of Search ............................. 435/123, 252.5, 435/252.1, 170

[56] References Cited

U.S. PATENT DOCUMENTS

| | | |
|---|---|---|
| 4,017,362 | 4/1977 | Miura et al. |
| 5,200,534 | 4/1993 | Rao ............................... 549/510 |
| 5,367,086 | 11/1994 | Rao. |

FOREIGN PATENT DOCUMENTS

| | | |
|---|---|---|
| WO 93/18018 | 9/1993 | WIPO. |
| WO 93/21338 | 10/1993 | WIPO. |

OTHER PUBLICATIONS

A. L. Lehninger, Biochemistry, 2nd Edition, Worth Pub. Inc., 1975, p. 256.

A. White, et al., Principles of Biochemistry, 6th Edition, 1978, pp. 16–18, McGraw Hill Publisher.

W. Boland, et al., Synthesis, "Esterolytic and Lipolytic Enzymes in Organic Synthesis", Dec., 1991, pp. 1049–1072.

E. Santaniello, et al., Chem. Rev., "The Biocatalytic Approach to the Preparation of Enantiomerically Pure Chiral Building Blocks", 1992, vol. 92, pp. 1071, 1094–1095.

L Ringel et al., The Journal of Pharmacology and Experimental Therapeutics, "Taxol is Converted to 7–Epitaxol, a Biologically Active Isomer in Cell Culture Medium", vol. 242, No. 2, pp. 692–698 (1987).

B. Monsarrat, et al., Drug Metabolism and Disposition, "Taxol Metabolism, Isolation and Identification of Three Major Metabolites of Taxol in Rat Bile", vol. 18, No. 6, pp. 895–901 (1990).

D. Kingston, Pharmac. Ther., "The Chemistry of Taxol", vol. 52, pp. 1–34, 1991.

G. Pedrocchi–Fantoni et al., J. Chem. Soc. Perkin Trans. 1, "Regio–and Chemo–selective Properties of Lipase from Candida cylindracea", 1992, pp. 1029–1033.

V. S. Parmar, et al., Tetrahedron, "Regioselective Deacylation of Polyacetoxy Aryl–methyl Ketones by Lipases in Organic Solvents", vol. 48, No. 31, pp. 6495–6498, 1992.

M. Berger et al., Biotechnology Letters, "Regioselectivity of Lipases in Organic Solvents", vol. 13, No. 5, pp. 333–338 (1991).

Bergy's Manual of Systematic Bacteriology, p. 356, vol. 1, Eds. Noel R. Krieg and John G. Holt (1989).

Bergy's Manual of Systematic Bacteriology, p. 1112, vol. 2, Eds. Peter H. A. Sneath et al. (1989).

Bergy's Manual of Systematic Bacteriology, p. 289, vol. 1, Eds. Noel R. Krieg and John G. Holt (1989).

Ogawa et al, Biosci., Biotech. Biochem. 56 (12), 1933–1936, 1992.

Nishitani et al, J. Biol. Chem, 266, pp. 6539–6543, 1991.

Blanco et al., Can J. Microbiol., 39: 1162–1166, 1993.

Paul et al. Lett. Appl. Microbiol., 1993, 16: 167–169.

Padmayeruma et al., Carbohydrate Research, vol. 250, pp. 79–86, 1992.

Zong et al, Agric. Biol. Chem. 53, 2129–2139, 1989.

Gooday, G.W. In "Microbial Polysaccharides and Polysaccharses", 1979, ASM.

*Primary Examiner*—Irene Marx
*Attorney, Agent, or Firm*—Suzanne E. Babajko

[57] ABSTRACT

An enzymatic hydrolysis method, wherein one or more C-7 sugar, preferably C-7 xylosyl-bearing taxanes are contacted with an enzyme or microorganism capable of hydrolyzing said sugar groups to hydroxyl groups.

12 Claims, No Drawings

ENZYMATIC HYDROLYSIS METHOD FOR THE CONVERSION OF C-7 SUGAR TO C-7 HYDROXYL TAXANES

This is a continuation of application Ser. No. 08/181,633 filed on Jan. 13, 1994, now abandoned.

1. Field of the Invention

The present invention relates to an enzymatic hydrolysis method for the conversion of C-7 sugar-bearing, especially C-7 xylosyl-bearing, taxanes to C-7 hydroxyl-bearing taxanes. The product compounds may be pharmacologically active taxanes such as paclitaxel and paclitaxel analogues, or may be compounds useful as intermediates in the preparation of such pharmacologically active taxanes.

2. Background of the Invention

Taxanes are diterpene compounds which find utility in the pharmaceutical field. For example, paclitaxel (Taxol®), a taxane having the structure:

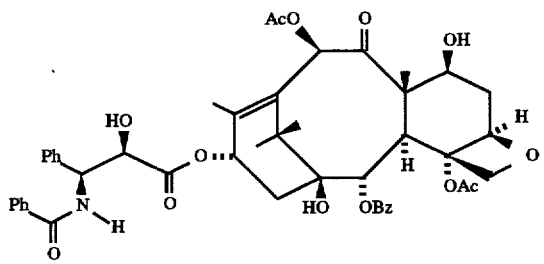

where Ph is phenyl, Ac is acetyl and Bz is benzoyl, has been found to be an effective anticancer agent.

Naturally occurring taxanes such as paclitaxel may be found in plant materials, and have been isolated therefrom. Such taxanes may, however, be present in plant materials in relatively small amounts so that, in the case of paclitaxel, for example, large numbers of the slow-growing yew trees forming a source for the compound may be required. The art has thus continued to search for synthetic, including semi-synthetic routes for the preparation of naturally occurring taxanes such as paclitaxel, as well as for the preparation of synthetic analogues thereof.

Taxanes having a hydroxyl group at C-7 are of particular interest, both as pharmacologically active final products (such as paclitaxel) and as intermediates for the semi-synthetic preparation of such pharmacologically active final products (such as baccatin III and 10-desacetylbaccatin III). However, taxanes may be obtained, such as by extraction of plant materials, which contain, for example, xylosyl groups bonded through a glycosidic linkage at C-7, rather than hydroxyl groups at that position. Methods for converting sugar-bearing, especially xylosyl-bearing taxanes to taxanes containing a hydroxyl group at C-7 would thus be useful in enhancing production of the aforementioned preferred hydroxyl compounds.

SUMMARY OF THE INVENTION

The present invention provides a method for the preparation of C-7 hydroxyl-bearing taxanes from the corresponding C-7 sugar-bearing, especially C-7 xylosyl-bearing, taxanes. In particular, the present invention provides a method for the preparation of at least one taxane containing a hydroxyl group directly bonded at C-7, comprising the steps of contacting at least one taxane containing a sugar group directly bonded at C-7 with an enzyme or microorganism capable of catalyzing the hydrolysis of said sugar group to a hydroxyl group, and effecting said hydrolysis.

DETAILED DESCRIPTION OF THE INVENTION

The present invention provides an efficient method for the preparation of C-7 hydroxyl-bearing taxanes from C-7 sugar-bearing taxanes. A single taxane may be hydrolyzed, or a mixture of different taxanes may be sequentially or simultaneously hydrolyzed, according to the method of the present invention. In a preferred embodiment, a mixture of taxanes, such as may be obtained by extraction of plant materials, is hydrolyzed according to the present method. The aforementioned mixture to be employed as the starting material may comprise, in addition to the one or more C-7 sugar-bearing taxanes to be hydrolyzed, taxanes containing groups other than sugar groups at C-7, such as hydroxyl. The present invention is described further as follows.

In a preferred embodiment, the present invention provides a method for the preparation of at least one C-7 hydroxyl-bearing taxane of the following formula I:

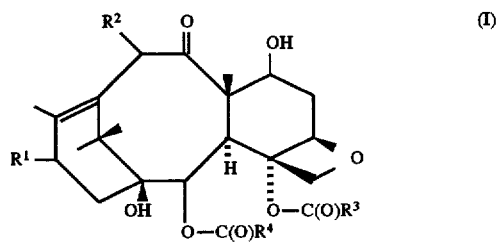

where
$R^1$ is hydroxyl or acyloxy, especially where $R^1$ has the structure of formula III described below;
$R^2$ is acyloxy (especially alkylcarbonyloxy) or hydroxyl; and
$R^3$ and $R^4$ are independently hydrogen, alkyl, alkenyl, alkynyl, cycloalkyl, cycloalkenyl, aryl, or heterocyclo;
or salts thereof, comprising the steps of contacting at least one C-7 sugar-bearing taxane of the following formula II:

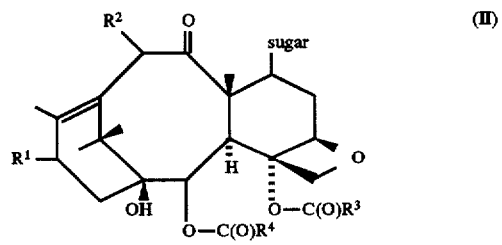

where
$R^1$, $R^2$, $R^3$ and $R^4$ are as defined above, and "sugar" is a sugar group directly bonded at C-7, or salts thereof, with an enzyme or microorganism capable of catalyzing the hydrolysis of said C-7 sugar group to a hydroxyl group, and effecting said hydrolysis.

All stereoconfigurations of the unspecified chiral centers of the compounds of the formulae I and II are contemplated in the hydrolysis method of the present invention, either alone (that is, substantially free of other stereoisomers) or in admixture with other stereoisomeric forms.

As indicated above, the present method is particularly useful where a mixture of taxanes is obtained, such as by extraction of plant materials yielding paclitaxel in admixture with other taxanes one or more of which contain a sugar group at C-7, and where a C-7 hydroxyl taxane such as paclitaxel is ultimately desired.

In the method of the present invention, the stereoconfiguration of the C-7 group of the starting taxane is preferably retained in the product. The C-7 substituent preferably has the same absolute stereoconfiguration as the C-7 hydroxyl group of paclitaxel.

Definitions

The terms "enzymatic process" or "enzymatic method", as used herein, denote a process or method of the present invention employing an enzyme or microorganism. The term "hydrolysis", as used herein, denotes the conversion of a sugar group to a hydroxyl group, and may be achieved, for example, by contact with water and/or a suitable organic alcohol according to the method of the present invention. Use of "an enzyme or microorganism" in the present method includes the use of two or more, as well as a single, enzyme or microorganism.

The term "sugar", as used herein, denotes mono-, di-, oligo- or polysaccharides, especially 5- and 6-membered ring sugars such as galactose, glucose, mannose, arabinose, ribose or, preferably, xylose, or disaccharides thereof such as xylosyl-xylose. The term "sugar group directly bonded at C-7" denotes a sugar bonded directly through a glycosidic linkage to the C-7 position of a taxane moiety. Preferred sugar groups are xylosyl groups having the structure:

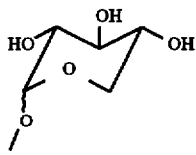

where the wavy line denotes either α, or preferably β, configurations.

The terms "alkyl" or "alk", as used herein alone or as part of another group, denote optionally substituted, straight and branched chain saturated hydrocarbon groups, preferably having 1 to 12 carbons in the normal chain. Exemplary unsubstituted such groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl and the like. Exemplary substituents may include one or more of the following groups: halo, alkoxy, alkylthio, alkenyl, alkynyl, aryl, cycloalkyl, cycloalkenyl, hydroxy or protected hydroxy, carboxyl (—COOH), alkyloxycarbonyl, alkylcarbonyloxy, carbamoyl ($NH_2$—CO—), amino (—$NH_2$), mono- or dialkylamino, or thiol (—SH).

The terms "lower alk" or "lower alkyl", as used herein alone or as part of another group, denote such optionally substituted groups as described above for alkyl having 1 to 4 carbon atoms in the normal chain.

The terms "alkoxy" or "alkylthio", as used herein alone or as part of another group, denote an alkyl group as described above bonded through an oxygen linkage (—O—) or a sulfur linkage (—S—), respectively. The term "alkyloxycarbonyl", as used herein alone or as part of another group, denotes an alkoxy group bonded through a carbonyl group. The term "alkylcarbonyloxy", as used herein alone or as part of another group, denotes an alkyl group bonded through a carbonyl group which is, in turn, bonded through an oxygen linkage. The terms "monoalkylamino" or "dialkylamino", as used herein alone or as part of another group, denote an amino group substituted by one or two alkyl groups as described above, respectively.

The term "alkenyl", as used herein alone or as part of another group, denotes such optionally substituted groups as described above for alkyl, further containing at least one carbon to carbon double bond. Exemplary substituents include one or more alkyl groups as described above, and/or one or more groups described above as alkyl substituents. The term "alkenyloxy", as used herein alone or as part of another group, denotes an alkenyl group as described above bonded through an oxygen linkage (—O—).

The term "alkynyl", as used herein alone or as part of another group, denotes such optionally substituted groups as described above for alkyl, further containing at least one carbon to carbon triple bond. Exemplary substituents include one or more alkyl groups as described above, and/or one or more groups described above as alkyl substituents. The term "alkynyloxy", as used herein alone or as part of another group, denotes an alkynyl group as described above bonded through an oxygen linkage (—O—).

The term "cycloalkyl", as used herein alone or as part of another group, denotes optionally substituted, saturated carbocyclic ring systems, preferably containing 1 to 3 rings and 3 to 7 carbons per ring. Exemplary unsubstituted such groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, and/or one or more groups described above as alkyl substituents. The term "cycloalkyloxy", as used herein alone or as part of another group, denotes a cycloalkyl group as described above bonded through an oxygen linkage (—O—).

The term "cycloalkenyl", as used herein alone or as part of another group, denotes such optionally substituted groups as described above for cycloalkyl, further containing at least one carbon to carbon double bond forming a partially unsaturated ring. Exemplary substituents include one or more alkyl groups as described above, and/or one or more groups described above as alkyl substituents. The term "cycloalkenyloxy", as used herein alone or as part of another group, denotes a cycloalkenyl group as described above bonded through an oxygen linkage (—O—).

The terms "ar" or "aryl", as used herein alone or as part of another group, denote optionally substituted, carbocyclic aromatic groups, preferably containing 1 or 2 rings and 6 to 12 ring carbons. Exemplary unsubstituted such groups include phenyl, biphenyl, and naphthyl. Exemplary substituents include one or more, preferably three or fewer, nitro groups, alkyl groups as described above and/or groups described above as alkyl substituents. The term "aryloxy", as used herein alone or as part of another group, denotes an aryl group as described above bonded through an oxygen linkage (—O—).

The terms "heterocyclo" or "heterocyclic", as used herein alone or as part of another group, denote optionally substituted fully saturated or unsaturated, aromatic or non-aromatic cyclic groups having at least one heteroatom in at least one ring, preferably monocyclic or bicyclic groups having 5 or 6 atoms in each ring. The heterocyclo group may, for example, have 1 or 2 oxygen atoms, 1 or 2 sulfur atoms, and/or 1 to 4 nitrogen atoms in the ring. Each heterocyclo group may be bonded through any carbon or heteroatom of the ring system. Exemplary heterocyclo groups include the following: thienyl, furyl, pyrrolyl, pyridyl, imidazolyl, pyrrolidinyl, piperidinyl, azepinyl, indolyl, isoindolyl, quinolinyl, isoquinolinyl, benzothiazolyl, benzoxazolyl, benzimidazolyl, benzoxadiazolyl, and benzofurazanyl. Exemplary substituents include one or more alkyl groups as described above and/or one or more groups described above as alkyl substituents. The term "heterocyclooxy", as used herein alone or as part of another group, denotes a heterocyclo group as described above bonded through an oxygen linkage (—O—).

The terms "halogen" or "halo", as used herein alone or as part of another group, denote chlorine, bromine, fluorine, and iodine.

The term "taxane", as used herein, denotes compounds containing a taxane moiety as described following. The term "taxane moiety", as used herein, denotes moieties containing the core structure (with numbering of ring system positions used herein shown):

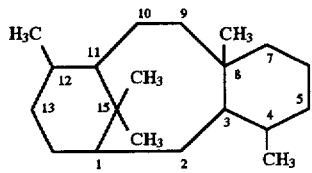

which core structure may be substituted and which may contain ethylenic unsaturation in the ring system thereof. Such moieties having an oxetane ring fused at the 4- and 5-positions, and an ethylenic double bond between C-11 and C-12, such as are found in paclitaxel, are preferred.

The term "hydroxy (or hydroxyl) protecting group", as used herein, denotes any group capable of protecting a free hydroxyl group which, subsequent to the reaction for which it is employed, may be removed without disturbing the remainder of the molecule. Exemplary such groups, and the synthesis thereof, may be found in "Protective Groups in Organic Synthesis" by T. W. Greene, John Wiley and Sons, 1981, or Fieser & Fieser.

The term "salt", as used herein, includes acidic and/or basic salts formed with inorganic and/or organic acids and bases.

The term "acyl", as used herein alone or as part of another group, denotes the moiety formed by removal of the hydroxyl group from the group —COOH of an organic carboxylic acid. The term "acyloxy", as used herein alone or as part of another group, denotes an acyl group as described above bonded through an oxygen linkage (—O—).

Starting Materials

The C-7 sugar-bearing taxanes employed as starting materials for the present invention may be any such compounds capable of undergoing the enzymatic hydrolysis method described herein. The starting materials are preferably xylosyl-bearing taxanes, which may be formed naturally, such as 7-xylosyltaxol, 7-xylosyl-10-desacetyltaxol, 7-xylosylbaccatin III, 7-xylosyl-10-desacetylbaccatin III, 7-xylosylcephalomannine, 7-xylosyl-10-deacetylcephalomannine, 7-xylosyltaxol C or 7-xylosyl-10-deacetyltaxol C, alone or in admixture with each other or other taxanes. "Naturally formed" taxane starting materials are preferably obtained by plant cell culture of, and/or extraction from, taxane-producing plant tissues, particularly tissues from, or derived from, plants of the Taxus genus such as Taxus baccata, Taxus cuspidata, Taxus brevifolia, Taxus wallichiana, Taxus media, Taxus hicksii, especially Taxus x. media hicksii. Exemplary plant tissues include the roots, needles, bark and whole seedling. For descriptions of and preferred methods of obtaining the C-7 xylosyl-bearing taxane starting materials of the present method see, for example, D. G. I. Kingston, Pharmac. Ther., Vol. 52, pp. 1–34 (1991); K. V. Rao, Pharmaceutical Research, Vol. 10, No. 4, pp. 521–524 (1993); and V. Senilh et al., J. Nat. Prod., 47, pp. 131–137 (1984).

C-7 sugar-bearing taxane starting materials for the present hydrolysis method may also be obtained by addition of a sugar group at the C-7 position of a taxane. One method for providing such materials is by the enzymatic conversion of a C-7 hydroxyl-bearing taxane to the corresponding taxane bearing a sugar group at C-7, which method is novel. Thus, the present invention further provides a method for the preparation of at least one taxane containing a sugar group directly bonded at C-7 (preferably a taxane of the above formula II), comprising the steps of contacting at least one taxane containing a hydroxyl group directly bonded at C-7 (preferably a taxane of the above formula I), in the presence of a sugar, with an enzyme or microorganism capable of catalyzing the conversion of said hydroxyl group to said sugar group at C-7, and effecting said conversion. The enzyme or microorganism employed may be any enzyme or microorganism capable of catalyzing the aforementioned conversion to a sugar group, and is preferably an enzyme or microorganism described below for use in the hydrolysis method of the present invention, but used under conditions favoring the reverse reaction. Reaction conditions such as reaction medium, temperature, pH etc. may also be selected from those described below for the enzymatic hydrolysis method of the present invention, although they may be modified, such as by minimizing the presence of water, to favor the addition of a sugar group.

In one embodiment, a C-7 sugar-bearing taxane may be prepared from the corresponding C-7 hydroxyl-bearing taxane by the enzymatic method described above, and the taxane so prepared modified as desired such as described further in the Utility section below, at a position other than C-7 during which the sugar group acts as a hydroxyl protecting group, followed by enzymatic hydrolysis according to the method of the present invention to yield a final taxane bearing a hydroxyl group directly bonded at C-7.

Enzymes and Microorganisms

The enzyme or microorganism employed in the hydrolysis method of the present invention may be any enzyme or microorganism capable of catalyzing the enzymatic hydrolysis method described herein. The enzymatic or microbial materials, regardless of origin or purity, may be employed in the free state or immobilized on a support such as by physical adsorption or entrapment.

Exemplary microorganisms include those within the following genera: Flavobacterium, Acinetobacter, Moraxella, Bacillus, Sporolactobacillus, Clostridium, Desulfotomaculum, Sporosarcina, Oscillospira, Planococcus, Lactobacillus, Kurthia, Micrococcus, Stomatococcus, Staphylococcus, Arthrobacter, Neisseria or Kingella. Preferred microorganisms are those species within the genera Micrococcus, such as *Micrococcus luteus, Micrococcus lylae, Micrococcus varians, Micrococcus roseus, Micrococcus agilis, Micrococcus kristinae, Micrococcus nishinomiyaensis, Micrococcus sedentarius*, or *Micrococcus halobius;* Bacillus, such as *Bacillus anchracis, Bacillus huringiensis, Bacillus mycoides, Bacillus fastidiosus, Bacillus circulans, Bacillus cereus, Bacillus insolitus, Bacillus lentus, Bacillus panothenticus, Bacillus alcalophilus, Bacillus megaterium, Bacillus sphaericus, Bacillus marinus, Bacillus ientimorbus, Bacillus pasceurii, Bacillus azotoformans, Bacillus macquariensis, Bacillus globisporus, Bacillus laterosporus, Bacillus popilliae, Bacillus firmus, Bacillus pumilus, Bacillus subtilis, Bacillus badius, Bacillus polymyxa, Bacillus alvei, Bacillus iicheniformis, Bacillus coagulans, Bacillus brevis, Bacillus stearothermophilus, Bacillus macerans, Bacillus acidocaldarius, Bacillus schlegelii,* or *Bacillus larvae;* Flavobacerium, such as *Flavobacterium acquatile, Flavobacterium breve, Flavobacterium balustinum, Flavobacterium meningosepticum, Flavobacterium odoratum, Flavobacterium multivorum,* or *Flavobacterium spiritivorum;* and, particularly, Moraxella, such as species of the subgenus Moraxella such as *Moraxella* (Moraxella) *lacunata*, *Moraxella* (Moraxella) *bovis*, *Moraxella* (Moraxella) *nonliquefaciens*, *Moraxella* (Moraxella) *atlantae*, *Moraxella* (Moraxella) *phenylpyruvica*, or *Moraxella* (Moraxella) *osloensis*, or species of the subgenus Branhamella such as *Moraxella* (Branhamella) *catarrhalis*, *Moraxella* (Branhamella) *caviae*, *Moraxella* (Branhamella) *ovis*, or *Moraxella* (Branhamella) *cuniculi*.

Especially preferred microorganisms are Moraxella sp. ATCC 55475, *Bacillus macerans* ATCC 55476, *Bacillus circulans* ATCC 55477, and Micrococcus sp. ATCC 55478. The term "ATCC" as used herein refers to the accession number of the American Type Culture Collection, 12301 Parklawn Drive, Rockville, Md. 20852, the depository for the organism referred to. The above microorganisms were deposited on Sep. 30, 1993.

The biologically pure microorganisms Moraxella sp. ATCC 55475, *Bacillus macerans* ATCC 55476, *Bacillus circulans* ATCC 55477, and Micrococcus sp. ATCC 55478 are novel microorganisms. It should be understood that mutants of these microorganisms are also contemplated by the present invention, for use in the hydrolysis method described herein, such as those modified by the use of chemical, physical (for example, ultraviolet radiation) or biological means (for example, by molecular biology techniques).

Moraxella sp. ATCC 55475 may be cultivated on a nutrient broth medium containing beef extract (3.0 g), peptone (10.0 g), sodium chloride (5.0 g), adjusted to pH 7.0 and sterilized for 20 minutes at 121° C. The characteristics of this microorganism are as follows: gram negative rods (1 to 2 μm); non-motile; non-spore forming; aerobic growth on a variety of media; catalase-positive and oxidase-positive only when tetramethyl-p-phenylenediamine is used (isolated from soil sample obtained from the Delaware Gap National Recreational Area, N.J.).

Bacillus macerans ATCC 55476 may be cultivated on a nutrient broth medium containing beef extract (3.0 g), peptone (10.0 g), sodium chloride (5.0 g), adjusted to pH 7.0 and sterilized for 20 minutes at 121° C. The characteristics of this microorganism are as follows: gram positive rods; motile; spore forming; aerobic growth on a variety of media; catalase-positive and oxidase-positive; weak glucose utilization; gelatin liquefaction (isolated from soil sample obtained from Arlington, Tx.).

*Bacillus circulans* ATCC 55477 may be cultivated on a nutrient broth medium containing beef extract (3.0 g), peptone (10.0 g), sodium chloride (5.0 g), adjusted to pH 7.0 and sterilized for 20 minutes at 121° C. The characteristics of this microorganism are as follows: gram positive rods; motile; spore forming; aerobic growth on a variety of media; catalase-positive and oxidase-positive; weak glucose utilization; does not liquify gelatin (isolated from wood sample obtained from Hamilton Square, N.J.).

Micrococcus sp. ATCC 55478 may be cultivated on a nutrient broth medium containing beef extract (3.0 g), peptone (10.0 g), sodium chloride (5.0 adjusted to pH 7.0 and sterilized for 20 minutes at 121° C. The characteristics of this microorganism are as follows: gram positive spherical coccus (0.5 to 1.5 μm) in diameter; cells occur in pairs, or clusters; non-motile; non-spore forming; aerobic growth on a variety of media; catalase- and oxidase-positive; glucose is fermented (isolated form soil sample obtained from Harriman Park, Tuxedo, N.Y.).

The present invention also provides a screening method for selecting microorganisms capable of the present enzymatic hydrolysis. A preferred method for selecting a microorganism capable of enzymatic hydrolysis of a starting C-7 sugar-bearing taxane according to the method of the present invention is by use of the following novel screening method, comprising the steps of:

(i) selecting a growth medium capable of supporting growth of the microorganism to be screened;
(ii) selecting an indicator glycoside;
(iii) contacting the microorganism with the growth medium of step (i) so that growth of the microorganism occurs, and with the indicator glycoside of step (ii);
(iv) observing the microorganism, in the presence of the indicator glycoside, to determine whether hydrolysis occurs; and
(v) testing the microorganism for hydrolysis of said C-7 sugar-bearing taxane.

The term "glycoside", as used herein, denotes a compound which may be formed by the reaction of an aldehyde or ketone group of a sugar with the hydroxyl group of an alcohol (which alcohol may also be a sugar) to form a glycosidic linkage (—O—), which compound forms as products, upon hydrolyric cleavage, the sugar and an aglycone (that is, the cleaved alcohol). The term "indicator glycoside", as used herein, denotes a glycoside wherein the aglycone fluoresces under ultraviolet light (for example, 4-methylumbelliferyl-beta-D-xylopyranoside) or changes color (for example, p-nitrophenyl-β-D xyloside) upon hydrolysis, thereby allowing a determination, by observing the microorganism in contact with the indicator glycoside, as to whether a given microorganism is capable of enzymatic hydrolysis. Preferably, the indicator glycoside is an indicator xyloside. Indicator xylosides with a bulky aglycone are preferred for the selection of microorganisms capable of hydrolyzing C-7 xylosyltaxanes.

In step (i) above, the growth medium preferably contains, as a carbon source, a glycoside such as xylan or other xyloside which is capable of being hydrolyzed at the glycosidic bond, so that the medium is enriched for organisms able to hydrolyze xylosidic bonds thereby facilitating selection thereof. In step (iii), the microorganisms may be contacted with the growth medium, for example, by plating dilute soil suspensions in water, containing the microorganism, onto agar growth medium. The microorganism may be contacted with the indicator glycoside, for example, by overlaying a soft agar containing the indicator glycoside onto a plate of growth medium where colonies of the microorganism have been allowed to grow, or by adding the indicator glycoside to the growth medium before placing the microorgansims in contact therewith.

After employing the rapid and efficient steps (i) to (iv) of the screening method of the present invention, colonies of the microorganism which are growing or have been grown may, in step (v), be contacted with a C-7 sugar-bearing taxane for a suitable incubation period to verify hydrolysis of the sugar group. For example, individual colonies may be removed from an agar plate and grown in small shake flasks with a 7-xylosyltaxane, the cells thereafter removed, and the products analyzed, such as by HPLC, to verify hydrolysis of the sugar group.

Exemplary enzymes for use in the present hydrolysis method are hydrolases, particularly glycosidases or glycanases. Preferred enzymes include those derived from microorganisms, particularly those microorganisms described above. Such enzymes may be isolated, for example, by extraction and purification methods.

Where microorganisms are employed, the cells may be used in the form of intact wet cells or dried cells such as lyophilized, spray-dried or heat-dried cells, or in the form of treated cell material such as ruptured cells or cell extracts. The use of genetically engineered organisms is also contemplated. The host cell may be any cell, e.g. *Escherichia coli*, modified to contain a gene or genes for expressing one or more enzymes capable of catalysis as described herein.

Where one or more microorganisms are employed, the enzymatic hydrolysis method of the present invention may be carried out subsequent to the fermentation of the microorganism (two-stage fermentation and hydrolysis), or concurrently therewith, that is, in the latter case, by in situ fermentation and hydrolysis (single-stage fermentation and hydrolysis).

Growth of the microorganisms may be achieved by one of ordinary skill in the art by the use of an appropriate medium. Appropriate media for growing microorganisms include those which provide nutrients necessary for the growth of the microbial cells. A typical medium for growth includes necessary carbon sources, nitrogen sources, and elements (e.g. in trace amounts). Inducers may also be added. The term "inducer", as used herein, includes any compound enhancing formation of the desired enzymatic activity within the microbial cell.

Carbon sources may include sugars such as maltose, lactose, glucose, fructose, glycerol, sorbitol, sucrose, starch, mannitol, propylene glycol, xylan and the like; salts of organic acids such as sodium acetate, sodium citrate, and the like; and alcohols such as ethanol, propanol and the like.

Nitrogen sources may include N-Z amine A, corn steep liquor, soy bean meal, beef extracts, yeast extracts, molasses, baker's yeast, tryprone, nutrisoy, peptone, yeastamin, amino acids such as sodium glutamate and the like, sodium nitrate, ammonium sulfate and the like.

Trace elements may include magnesium, manganese, calcium, cobalt, molybdenum, copper, nickel, iron, sodium and potassium salts. Phosphates may also be added in trace, or preferably, greater than trace amounts.

The medium employed may include more than one carbon or nitrogen source or other nutrient.

Preferred media for growth include aqueous media, such as those described in the Examples herein.

The agitation and aeration of the reaction mixture affects the amount of oxygen available during growth. The agitation range from 100 to 250 RPM is preferred; aeration of about 1 to 10 volumes of air per volume of media per minute is preferred.

For growth of the microorganisms and/or hydrolysis according to the method of the present invention, the pH of the medium is preferably from about 4 to about 8.5, and the temperature is preferably from about 24° C. to about 37° C. Hydrolysis may, for example, be carried out in vitro over time periods such as 1 to 72 hours, or preferably until the yield of desired product is maximized. Preferably, during hydrolysis, the pH is kept at or below 7 such as where it is desirable to minimize epimerization at C-7 (for example, where 10-deacetyltaxol or 10-deacetylbaccatin III are present). It is preferred to conduct the hydrolysis of the present invention at a pH of from 4 to 7, particularly under non-basic conditions.

It is also preferred to employ an aqueous liquid as the hydrolysis reaction medium, although an organic liquid, or a miscible or immiscible (biphasic) organic/aqueous liquid mixture, may also be employed. It is preferred to employ 0.0025 to 2.5 weight % of the C-7 sugar-bearing taxane starting material(s) based on the combined weight of starting material(s) and hydrolysis reaction medium.

The amount of enzyme or microorganism employed relative to the starting material is selected to allow catalysis of the enzymatic hydrolysis of the present invention. It is preferred to obtain yields in excess of 90% (% C-7 hydrolyzed product obtained based on the starting C-7 sugar-bearing taxane) when employing the hydrolysis method of the present invention. Hydrolysis may be obtained selectively at C-7 of the starting taxane. That is, product(s) the greater portion (such as solely) of which are hydrolyzed at C-7 only may be obtained without hydrolysis at other positions.

Separation

The C-7 hydroxyl-bearing products of the processes of the present invention, and other taxane products such as those described below, may be isolated and purified, for example, by methods such as extraction, distillation, crystallization, and column chromatography.

Utility

Taxanes are diterpene compounds containing a taxane moiety as described above. Of particular interest are taxanes containing a taxane moiety in which the 13-position contains a sidechain, which taxanes are exemplified by paclitaxel. Pharmacologically active taxanes such as paclitaxel may be used as antitumor agents to treat patients suffering from cancers such as breast, ovarian, colon or lung cancers, melanoma and leukemia.

The compounds obtained by the hydrolysis method of the present invention are particularly useful either as pharmacologically active taxanes per se (such as paclitaxel), or as intermediates in the preparation of the aforementioned pharmacologically active taxanes. Thus, for example, where the compounds prepared by the methods of the present invention also bear a hydroxyl group at C-13 (for example, baccatin III or 10-desacetylbaccatin III), such compounds may be coupled with C-13 acyloxy sidechain-forming intermediate compounds, such as β-lactams, to obtain C-13 acyloxy sidechain-bearing taxanes such as paclitaxel or analogues thereof. The C-7 hydroxyl-bearing compounds prepared according to the methods of the present invention may optionally be modified prior to use in such C-13 acyloxy sidechain coupling. For example, one or more hydroxyl groups at positions other than C-13 may be protected prior to coupling and, thereafter, deprotected. In addition, modification at C-13 according to U.S. patent application Ser. No. 08/077,979 by Hanson et al., filed Jun. 15, 1993 (Attorney Docket No. LD58) (enzymatic hydrolysis of acyloxy to hydroxyl at C-13), and/or modification at C-10 according to U.S. patent application Ser. No. 08/077,980 by Hanson et al., filed Jun. 15, 1993 (Attorney Docket No. LD59) (enzymatic hydrolysis of acyloxy to hydroxyl, or enzymatic esterification of hydroxyl to acyloxy, at C-10), both incorporated hereinby reference, may be conducted prior to, during, or after the method of the present invention is employed.

The C-7 hydroxyl-bearing taxanes obtained by the hydrolysis method of the present invention, optionally modified as above, may, for example, be used in the preparation of C-13 acyloxy sidechain-bearing taxanes such as those recited, and prepared by the methods described in, European Patent Publication No. 400,971, U.S. Pat. No. 4,876,399, U.S. Pat. No. 4,857,653, U.S. Pat. No. 4,814,470, U.S. Pat. No. 4,924,012, U.S. Pat. No. 4,924,011, and Kingston, *Pharm. Ther.*, Vol. 52, 1–34 (1991), especially U.S. patent application Ser. No. 07/995,443, filed Dec. 23, 1992 by Poss et al. (Attorney Docket No. LD60), U.S. patent application Ser. No. 08/033,598, filed Mar. 19, 1993 by Thottathil et al. (Attorney Docket No. LD57), and U.S. patent application Ser. No. 08/154,840, filed Nov. 24, 1993, all incorporated hereinby reference.

Preferred Compounds

It is preferred to employ taxanes of the formula II or salts thereof in the hydrolysis method of the present invention, whereby enzymatic hydrolysis provides the corresponding compounds of the formula I or salts thereof.

In formulae I and II, $R^2$ is preferably hydroxyl or $R^5$—C(O)—O—, especially where $R^5$ is alkyl such as methyl; $R^3$ is preferably alkyl such as methyl; $R^4$ is preferably aryl such as phenyl; and $R^1$ is preferably hydroxyl or a group of the following formula III:

$$\begin{array}{c} R^6(O)CNH \quad\quad O \\ \diagdown \quad \diagup \\ R^7 \quad\quad O- \\ | \\ OR^8 \end{array} \quad (III)$$

where $R^6$ and $R^7$ are independently alkyl, alkoxy, alkenyl, alkenyloxy, alkynyl, alkynyloxy, cycloalkyl, cycloalkyloxy, cycloalkenyl, cycloalkenyloxy, aryl, aryloxy, heterocyclo or heterocyclooxy; and $R^8$ is hydrogen, alkyloxycarbonyl or a hydroxyl protecting group.

Exemplary taxanes of the formula II are 7-xylosyltaxol, 7-xylosyl-10-desacetyltaxol, 7-xylosylbaccatin III, 7-xylosyl-10-desacetylbaccatin III, 7-xylosyl cephalomannine, 7-xylosyl-10-deacetylcephalomannine, 7-xylosyl taxol C, or 7-xylosyl-10-deacetyltaxol C. Exemplary taxanes of the formula I are paclitaxel, 10-desacetyltaxol, baccatin III, 10-desacetylbaccatin III, cephalomannine, 10-deacetylcephalomannine, taxol C, or 10-deacetyltaxol C.

Paclitaxel is preferably ultimately prepared by the methods described herein.

Salts or solvates such as hydrates of reactants or products may be employed or prepared as appropriate in any of the methods of the present invention.

The present invention is further described by the following examples which are illustrative only, and are in no way intended to limit the scope of the present claims.

EXAMPLE 1

Selection of Xylosidases

Agar plates were prepared which contained 1% xylan from birchwood, 0.1% yeast extract, 0.1% tryptone and 1.5% agar. 2 g soil samples or rotting wood sample were suspended in 40 ml water, and 0.1 ml of a 1:200 dilution was spread per plate. The plates were incubated at room temperature (about 22° C.) for 1 week, then stored at 4° C. for 2 weeks. The plates were overlaid with 4 ml 0.8 % agarose (about 40° C.) containing 1 mM 4-methylumbelliferyl-beta-D-xylopyranoside. 125 colonies, fluorescent under long UV light, were picked and incubated for 3 days on plates at 28° C.

Shake flasks contained 1% milan from birchwood, 0.2% tryptone, 0.2% yeast extract and sufficient potassium phosphate to adjust to pH 7. The flasks were inoculated with a loopful of culture from a plate and incubated at 28° C. and 175 rpm. After 2 days, 1 mg 7-xylosyl-10-desacetyltaxol in 0.2 ml methanol was added and incubation was continued for 2 days. Another group of isolates was incubated for 1 day before addition of 7-xylosyl-10-desacetyltaxol and for 3 days after addition. 10 ml methanol was added to each flask, and the samples were assayed for 7-xylosyl-10-desacetyltaxol and 10-desacetyltaxol by HPLC Method 1 (described following). Of 86 isolates screened, 9 produced detectable amounts of 10-desacetyltaxol. The highest concentration of 10-desacetyltaxol was obtained with Moraxella sp. ATCC 55475 which was purified by restreaking and used in the Examples below.

EXAMPLE 2

Hydrolysis of 7-Xylosyl-10-desacetyltaxol 1 liter of medium in a 4 L Erlenmeyer flask containing 1% birchwood xylan, 0.2% tryptone, 0.2% yeast extract, 0.1% $KH_2PO_4$ and 0.1% $K_2HPO_4$ at pH 7 was inoculated with a 10 ml culture of Moraxella sp. ATCC 55475 and shaken for 3 days at 28° C. Cells were collected by centrifugation, washed with 50 ml 50 mM potassium phosphate buffer pH 7, centrifuged and resuspended in 30 ml of this buffer (0.122 g wet cells per ml). To 1.5 ml cell suspension was added 0.5 mg 7-xylosyl-10-desacetyltaxol in 0.2 ml methanol and 0.3 ml water. The suspension was mixed end-over-end at 12 rpm for 21 hours at 28° C.; the reaction was then stopped with 2 ml methanol and a sample was assayed by HPLC Method 1. No 7-xylosyl-10-desacetyltaxol remained and 0.230 mg/ml 10-desacetyltaxol was found (107% yield).

The reaction of this Example is illustrated as follows.

7-β-Xylosyl-10-desacetyltaxol

↓ Xylosidase

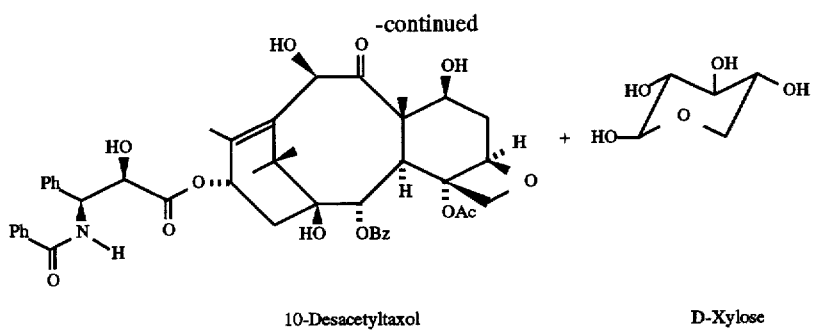

10-Desacetyltaxol         D-Xylose

EXAMPLE 3

Hydrolysis of 7-Xylosyltaxol

To a 1.5 ml cell suspension prepared as in Example 2 was added 0.5 mg 7-xylosyltaxol in 0.2 ml methanol and 0.3 ml water. The suspension was mixed end-over-end at 12 rpm for 21 hours at 28° C.; the reaction was then stopped with 2 ml methanol and a sample was assayed by HPLC Method 1. 0.011 mg/ml 7-xylosyltaxol remained and 0.167 mg/ml taxol was found (77% yield).

HPLC Method 1[1]

Column: Hewlett Packard hypersil 5 micron ODS C18 200×4.6 mm

Mobile phase: 60% methanol, 40% water

Flow rate: 1 ml/min

Column temperature: ambient

Detection wavelength: 235 nm

[1] B. Monsarrat, E. Mariel, S. Cros, M. Gares, D. Guenard, F. Gueritte-Voegelein, and M. Wright, *Drug Metabolism and Disposition*, 18, 895–901 (1990).

EXAMPLE 4

Hydrolysis of 7-Xylosylbaccain-III

Moraxella sp. ATCC 55475 was grown in shake flasks at 28° C. on media containing at pH 7: 2% glycerol, 0.2% tryprone, 0.2% yeast extract, 0.1% $K_2HPO_4$, 0.1% $KH_2PO_4$, 0.02% $MgSO_4 \cdot 7H_2O$, 0.001% NaCl, 0.001% $FeSO_4 \cdot 7H_2O$, and 0.001% $MnSO_{4.4}H_2O$. A 1 ml vial was used to inoculate 100 ml medium. After 4 days, 15 ml portions of this culture were used to inoculate 1 L medium in a 4 L erlenmeyer flask. After 3 days, cells were harvested by centrifugation, washed with 50 mM potassium phosphate buffer pH 7, centrifuged again and stored frozen.

1 mg 7-xylosyltaxol, 200 mg (108 milliunits) C-13 deacylase from *Nocardioides albus* ATCC 55425 (described in U.S. Ser. No. 08/077,979 discussed above), 0.2 ml methanol, 0.2 ml 1 M potassium phosphate buffer pH 7, and 3.6 ml water were mixed end-over-end at 48 rpm for 17 hours at 24° C. After 15 hours, HPLC analysis by Method 1 (described above) showed complete removal of C-13 side chain from the substrate. 2 ml of the solution now containing 7-xylosylbaccatin-III was added to 1 ml of the above Moraxella sp. cells (0.24 g wet cell weight) in 50 mM potassium phosphate buffer pH 7 and mixed end-over-end for 24 hours at 48 rpm. Reaction mixtures were extracted with 6 ml $CH_2Cl_2$. Extracts were dried and redissolved in methanol for HPLC analysis by Method 1. 0.101 mg/ml baccatin-III was found (102% yield based on initial 7-xylosyltaxol concentration).

EXAMPLE 5

Hydrolysis of 7-Xylosyl-10-deacetylbaccatin-III

Cells were prepared as described in Example 4. 1 mg 7-xylosyl-10-deacetyltaxol, 200 mg (108 milliunits) C-13 deacylase (described in Example 4), 0.2 ml methanol, 0.2 ml 1 M potassium phosphate buffer pH 7, and 3.6 ml water were mixed end-over-end at 48 rpm for 17 hours at 24° C. After 15 hours, HPLC analysis by Method 1 showed complete removal of C-13 side chain from the substrate. 2 ml of the solution now containing 7-xylosyl-10-deacetylbaccatin-III was added to 1 ml of the above Moraxella sp. cells (0.24 g wet cell weight) in 50 mM potassium phosphate buffer pH 7 and mixed end-over-end for 24 hours at 48 rpm. Reaction mixtures were extracted with 6 ml $CH_2Cl_2$. Extracts were dried and redissolved in methanol for HPLC analysis by Method 1. 0.099 mg/ml 10-deacetylbaccatin-III was found (103% yield based on initial 7-xylosyl-10-deacetyltaxol concentration).

EXAMPLE 6

Hydrolysis of 7-Xylosyl-10-deacetyltaxol by Subcellular Fractions

Moraxella sp. ATCC 55475 was shaken for 3 days at 28° C. in 6 4 L Erlenmeyer flasks each containing 1 L of the medium described in Example 2. The medium was treated with 2 ml/L Novo SP431 xylanase for 2 days at 28° C. to partially digest the xylan before inoculation. Cells were collected by centrifugation, washed with 50 mM potassium phosphate buffer pH 7, centrifuged again, then brought to a volume of 210 ml with this buffer. Cells were disrupted by sonication, centrifuged 20 min at 27504 × g, then the supernatant was centrifuged 20 min at 47807 × g. 17 ml of the 47807 × g supernatant was centrifuged 1 hour at 100,100 × g and the 100,100 × g pellet was resuspended in 17 ml of 50 mM potassium phosphate buffer pH 7. The protein concentration in the 100,100 × g supernatant was 4.72 mg/ml and in the resuspended pellet was 1.65 mg/ml. 0.5 mg 7-xylosyl-10-deacetyltaxol in 0.1 ml methanol was added to 1.9 ml pellet or supernatant fraction and the tubes were incubated for 15 hours at 25° C. Reactions were stopped by addition of 2 ml methanol and analyzed by HPLC Method 1.

The results obtained were as follows:

| Sample | Product 10-deacetyltaxol mg/ml | Substrate 7-xylosyl-10-deacetyltaxol mg/ml | Yield of 10-deacetyltaxol % |
| --- | --- | --- | --- |
| no enzyme | 0.000 | 0.256 | |
| supernatant | 0.038 | 0.237 | 18 |
| pellet | 0.206 | 0.038 | 96 |

EXAMPLE 7

Hydrolysis of Yew Extract

Moraxella sp. ATCC 55475 was grown in shake flasks as described in Example 4. Cells were collected and washed as described in Example 6, then disrupted by 2 passes through a microfluidizer at 12,000 psi. Unbroken cells were removed by centrifugation for 20 min at 27504 × g. The supernatant was centrifuged 1 hour at 100,100 × g and the 100,100 × g pellet was resuspended in 50 mM potassium phosphate buffer pH 7 at a protein concentration of 17 mg/ml. 0.05 ml 1 M potassium phosphate buffer, pH 7, 0.2 ml ethanolic extract of Taxus Hicksii seedlings, 20 mg polyvinylpolypyrrolidone (to remove inhibitory plant phenolics) and 0.75 ml water were mixed for 1 hour at 12 rpm and 25° C. 1 ml pellet suspension or 1 ml 50 mM potassium phosphate buffer pH 7 was added and incubation was continued for 3 days at 12 rpm and 25° C.

Samples were analyzed by HPLC Method 2 (described below) and the following results were obtained:

| Sample | Product 10-deacetyltaxol mg/ml | Substrate 7-xylosyl-10-deacetyltaxol mg/ml |
| --- | --- | --- |
| no enzyme | .020 | .020 |
| 100,100 × g pellet | .028 | .009 |

HPLC Method 2

Column: Phase Separations Inc. (Norwalk, Conn.) microbore spherisorb phenyl 150×2.0 mm, 3 micron Mobile phase: Solvent A:15 mM $KH_2PO_4$, adjusted to pH 4 with trifluoroacetic acid. Solvent B: acetonitrile

| Time/Minute | Solvent A (%) | Solvent B (%) |
| --- | --- | --- |
| 0 | 75 | 25 |
| 20 | 55 | 45 |
| 23 | 40 | 60 |
| 24 | 25 | 75 |
| 28 | 75 | 25 |

Column temperature: 35° C.

Detection wavelength: 230 nm.

What is claimed is:

1. A method for the preparation of at least one taxane of the following formula I containing a hydroxyl group directly bonded at C-7:

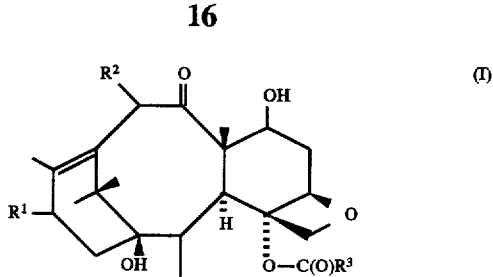

where
$R^1$ is hydroxyl or acyloxy;
$R^2$ is acyloxy or hydroxyl; and
$R^3$ and $R^4$ are independently alkyl or aryl;
or a salt thereof,
comprising the steps of contacting at least one taxane of the following formula II containing a xylosyl group directly bonded at C-7:

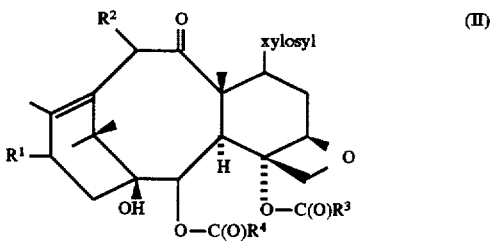

where
$R^1$, $R^2$, $R^3$ and $R^4$ are as defined above, and "xylosyl" is a xylosyl group directly bonded at C-7, or a salt thereof, with a microorganism, or an enzyme obtained therefrom, capable of catalyzing the hydrolysis of said C-7 xylosyl group to said C-7 hydroxyl group, effecting said hydrolysis, and obtaining said at least one taxane containing a hydroxyl group directly bonded at C-7, wherein said microorganism belongs to a genus selected from the group consisting of Moraxella, Micrococcus and Bacillus.

2. The method of claim 1, wherein said taxane of the formula II is at least one taxane selected from the group consisting of 7-xylosyltaxol, 7-xylosyl-10-desacetyltaxol, 7-xylosylbaccatin III, 7-xylosyl-10-desacetylbaccatin III, 7-xylosyl cephalomannine, 7-xylosyl-10-deacetylcephalomannine, 7-xylosyltaxol C, and 7-xylosyl-10-deacetyltaxol C; and said taxane of the formula I is at least one taxane selected from the group consisting of paclitaxel, 10-desacetyltaxol, baccatin III, 10-desacetylbaccatin III, cephalomannine, 10-deacetylcephalomannine, taxol C, and 10-deacetyltaxol C.

3. The method of claim 1, wherein the xylosyl-bearing taxane starting material employed in said hydrolysis method comprises a mixture of xylosyl-bearing taxanes.

4. The method of claim 3, wherein said mixture of manes is obtained by plant cell culture of plant tissue, wherein said plant is a member of the Taxus genus.

5. The method of claim 1, wherein a microorganism is employed which belongs to one of the following genera: Moraxella, Micrococcus or Bacillus.

6. The method of claim 5, wherein said microorganism is selected from the group consisting of Moraxella sp. ATCC 55475, Bacillus macerans ATCC 55476, Bacillus circulans ATCC 55477, and Micrococcus sp. ATCC 55478.

7. The method of claim 1, wherein an enzyme is employed which is obtained from a microorganism belonging to one of the following genera: Moraxella, Micrococcus or Bacillus.

8. The method of claim 7, wherein said enzyme is obtained from a microorganism selected from the group consisting of Moraxella sp. ATCC 55475, *Bacillus macerans* ATCC 55476, *Bacillus circulans* ATCC 55477, and Micrococcus sp. ATCC 55478.

9. The method of claim 1, wherein (i) the taxane product obtained by said method is paclitaxel, or (ii) the taxane product obtained by said method is an intermediate useful for paclitaxel synthesis and said method comprises the further step of converting said intermediate to paclitaxel.

10. The method of claim 3, wherein said mixture of taxanes is obtained by extraction from plant tissue, wherein said plant is a member of the Taxus genus.

11. The method of claim 1, wherein (i) the taxane product obtained by said method is a C-13 acyloxy sidechain-bearing taxane, or (ii) the taxane product obtained by said method is an intermediate useful for the synthesis of a C-13 acyloxy sidechain-bearing taxane and said method comprises the further step of converting said intermediate to a C-13 acyloxy sidechain-bearing taxane.

12. The method of claim 2, wherein said taxane of the formula I is at least one taxane selected from the group consisting of paclitaxel, baccatin III, 10-desacetyl baccatin III and cephalomannine.

* * * * *

UNITED STATES PATENT AND TRADEMARK OFFICE
CERTIFICATE OF CORRECTION

PATENT NO : 5,700,669

DATED : December 23, 1997

INVENTOR(S): Ronald L. Hanson, et al.

It is certified that error appears in the above-identified patent and that said Letters Patent is hereby corrected as shown below:

Column 16, line 55, "manes" should read --taxanes--.

Signed and Sealed this

Thirty-first Day of March, 1998

Attest:

BRUCE LEHMAN

Attesting Officer  Commissioner of Patents and Trademarks